United States Patent
Eckert et al.

(10) Patent No.: US 6,513,393 B1
(45) Date of Patent: Feb. 4, 2003

(54) CORIOLIS MASS/FLOW DENSITY METER

(76) Inventors: Gerhard Eckert, Angerstrasse 25, 79618 Rheinfelden (DE); Roman Häberli, Grossackerstrasse 13, CH-4566 Halten (CH); Christian Matt, Bahnhofstrasse 28, CH-4147 Aesch (CH); Alfred Wenger, Schulstrasse 170, CH-8413 Neftenbach (CH)

( * ) Notice: Subject to any disclaimer, the term of this patent is extended or adjusted under 35 U.S.C. 154(b) by 0 days.

(21) Appl. No.: 09/453,431

(22) Filed: Dec. 2, 1999

Related U.S. Application Data
(60) Provisional application No. 60/120,797, filed on Feb. 19, 1999.

(30) Foreign Application Priority Data

Dec. 11, 1998 (EP) .............................................. 98123680

(51) Int. Cl.[7] ................................................. G01F 1/84
(52) U.S. Cl. ................................................. 73/861.357
(58) Field of Search ..................... 73/861.357, 861.355, 73/861.55, 861.38, 861.356

(56) References Cited

U.S. PATENT DOCUMENTS

| | | |
|---|---|---|
| 4,187,721 A | 2/1980 | Smith |
| 4,491,025 A | 1/1985 | Smith et al. |
| 4,660,421 A | 4/1987 | Dahlin et al. |
| 4,711,132 A | 12/1987 | Dahlin |
| 4,733,569 A | 3/1988 | Kelsey et al. |
| 4,768,384 A | 9/1988 | Flecken et al. |

(List continued on next page.)

FOREIGN PATENT DOCUMENTS

| | | |
|---|---|---|
| DE | 196 34 663 | 3/1997 |
| EP | 0 375 300 | 6/1990 |
| EP | 0 701 107 | 3/1996 |
| EP | 0 759 542 | 2/1997 |
| EP | 0 831 306 | 3/1998 |
| EP | 0 849 568 | 6/1998 |
| WO | WO 98/02725 | 1/1998 |

OTHER PUBLICATIONS

Process Measurement and Analysis, from *Instrument Engineers' Handbook,* 3rd Ed., Béla G. Lipták, Editor–in–Chief, CRC Press LLC, 1999 (pages: Cover and copyright p.; 121–138).

Mass Flowmeters, from *Flow Measurement,* D. W. Spitzer, Editor, Instrument Society of America, 1991 (pages: Cover and copyright p.; 221, 235, 247).

Coriolis meters, from *Hydrocarbon Asia,* Mar. 1996, p. 79.

TRIO–MASS + TRU–MASS . . . the competent DUO, 1 page, undated, source unknown.

*Primary Examiner*—Benjamin R. Fuller
*Assistant Examiner*—Jewel V. Thompson
(74) *Attorney, Agent, or Firm*—Bose McKinney & Evans LLP

(57) ABSTRACT

The present Coriolis mass/flow density meter and method for measuring a mass flow rate of a medium flowing through a flow tube of a Coriolis mass flow meter provide measurement results which are independent of the current velocity field of the medium to be measured. At least one measuring tube is provided, through which the medium flows, which oscillates during operation. A means for measuring the oscillations is arranged at an inlet end of the measuring tube and provides a measurement signal. A second means for measuring the oscillations is arranged at the outlet of the measuring tube and provides a second measurement signal. A third measuring means provides a third measurement signal which represents the current Reynolds number of the flowing medium, Evaluation electronics generate a measurement value representing the mass through-flow. The evaluation electronics also generate a measurement value representing the current density of the medium.

31 Claims, 7 Drawing Sheets

U.S. PATENT DOCUMENTS

| | | |
|---|---|---|
| 4,801,897 A | 1/1989 | Flecken |
| 4,876,879 A | 10/1989 | Ruesch |
| 4,949,583 A | 8/1990 | Lang et al. |
| 5,218,873 A | 6/1993 | Lang |
| 5,307,689 A * | 5/1994 | Nishiyama et al. ...... 73/861.38 |
| 5,347,874 A * | 9/1994 | Kalotay et al. .......... 73/861.38 |
| 5,448,921 A * | 9/1995 | Van Cleve et al. ...... 73/861.52 |
| 5,473,949 A | 12/1995 | Cage et al. |
| 5,497,665 A | 3/1996 | Cage et al. |
| 5,576,500 A * | 11/1996 | Cage et al. ............ 73/861.357 |
| 5,648,616 A | 7/1997 | Keel |
| 5,661,232 A * | 8/1997 | Van Cleve et al. ........ 73/54.05 |
| 5,736,653 A | 4/1998 | Drahm et al. |
| 5,831,178 A | 11/1998 | Yoshimura et al. |
| 6,227,059 B1 * | 5/2001 | Schott et al. .......... 73/861.356 |

\* cited by examiner

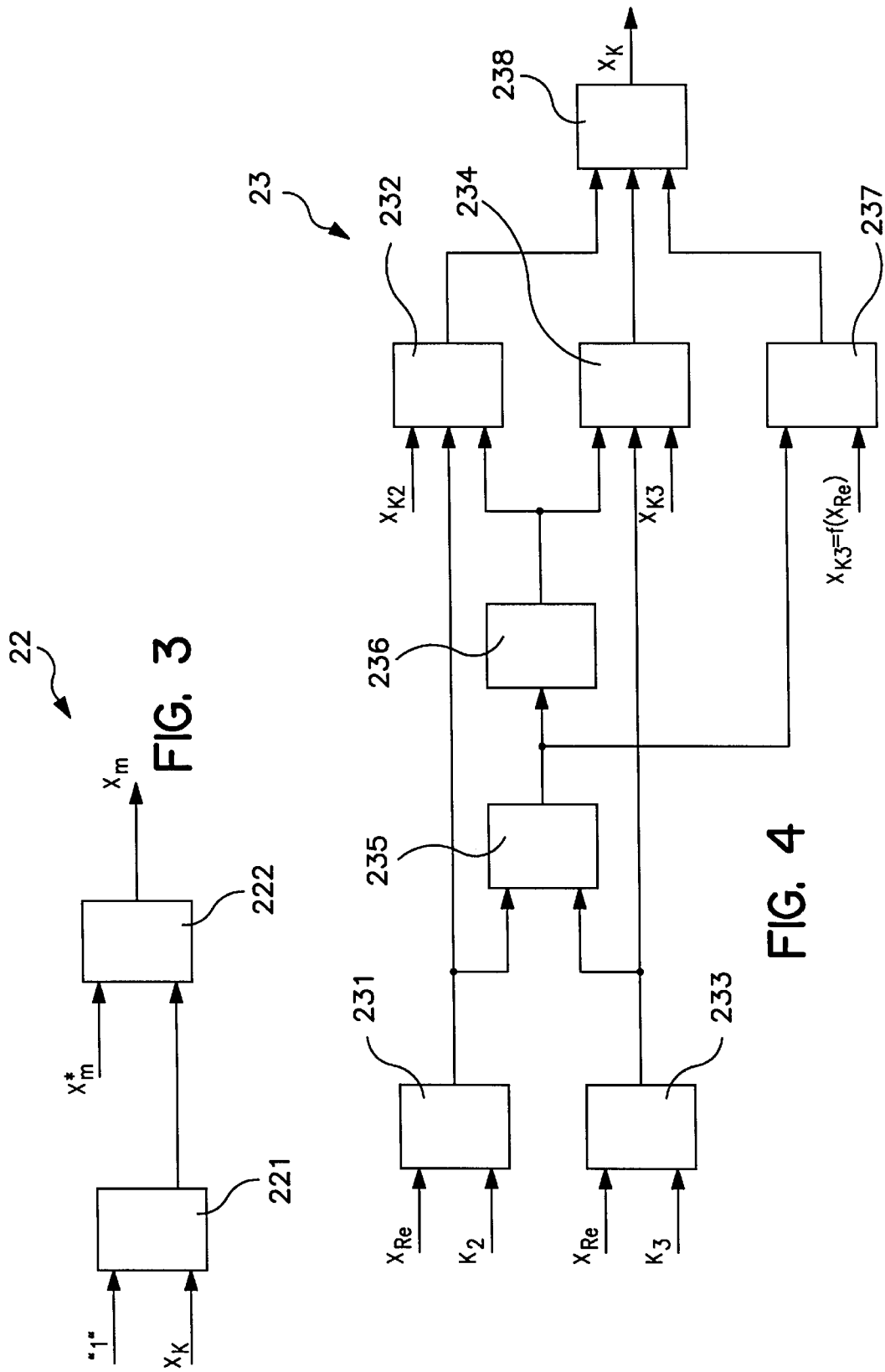

CORIOLIS MASS/FLOW DENSITY METER

This Application claim benefit to provisional Application No. 60/120,797 Feb. 19, 1999.

FIELD OF THE INVENTION

This invention relates to a Coriolis mass flow/density meter for media flowing through a pipe and to a method of generating a measured value representative of mass flow rate.

BACKGROUND OF THE INVENTION

In Coriolis mass flow/density meters for media flowing through a pipe, the measurement of the mass flow rate is based on the principle of causing a medium to flow through a flow tube inserted in the pipe and vibrating during operation, whereby the medium is subjected to Coriolis forces. The latter cause inlet-side and outlet-side portions of the flow tube to vibrate out of phase with respect to each other. The magnitude of these phase differences is a measure of the mass flow rate. The vibrations of the flow tube are therefore sensed by means of two vibration sensors positioned at a given distance from each other along the flow tube, and converted by these sensors into measurement signals from whose phase difference the mass flow rate is derived.

U.S. Pat. No. 4,187,721 discloses a Coriolis mass flow meter comprising:

- a single U-shaped flow tube having an inlet-side end and an outlet-side end, through which flow tube a medium flows during operation;
- a support means fixed to an inlet-side end and an outlet-side end of the flow tube such that the flow tube is capable of being vibrated;
- a vibration exciter which sets the flow tube into vibration during operation;
- a first measuring means positioned on the inlet-side of the flow tube for measuring the vibrations and for delivering a first measurement signal during operation;
- a second measuring means positioned on the outlet-side of the flow tube for measuring the vibrations and for delivering a second measurement signal during operation; and
- evaluation electronics for delivering, during operation,
- a first measured value representative of mass flow rate which is derived from the first and second measurement signals.

Further EP-A 849 568 (corresponding to U.S. Ser. No. 08/940,644, filed Sep. 30, 1997) discloses a Coriolis mass flow meter comprising:

- a single straight flow tube having an inlet-side end and an outlet-side end, through which flow tube a medium flows during operation;
- a support means fixed to an inlet-side end and an outlet-side end of the flow tube such that the flow tube is capable of being vibrated;
- a vibration exciter which sets the flow tube into vibration during operation;
- a first measuring means positioned on the inlet-side of the flow tube for measuring the vibrations and for delivering a first measurement signal during operation;
- a second measuring means positioned on the outlet-side of the flow tube for measuring the vibrations and for delivering a second measurement signal during operation; and
- evaluation electronics for delivering, during operation,
- a measured value representative of mass flow rate which is derived from the first and second measurement signals.

In addition each of U.S. Pat. Nos. 4,660,421 and 4,733,569 discloses a Coriolis mass flow meter comprising:

- a spiraled flow tube having an inlet-side end and an outlet-side end, through which flow tube a medium flows during operation;
- a support means fixed to an inlet-side end and an outlet-side end of the flow tube such that the flow tube is capable of being vibrated;
- a vibration exciter which sets the flow tube into vibration during operation;
- a first measuring means positioned on the inlet-side of the flow tube for measuring the vibrations and for delivering a first measurement signal during operation;
- a second measuring means positioned on the outlet-side of the flow tube for measuring the vibrations and for delivering a second measurement signal during operation; and
- evaluation electronics for delivering, during operation,
- a measured value representative of mass flow rate which is derived from the first and second measurement signals.

Furthermore each of U.S. Pat. Nos. 4,491,025, 4,660,421 and 5,218,873 discloses a Coriolis mass flow meter with two communicating flow tubes through which a medium flows during operation. These flow tubes are interconnected by means of an inlet-side first manifold having an inlet-side first end and an outlet-side second manifold having an outlet-side second end and are fixed by a support means such that the flow tube is capable of being vibrated.

Both U.S. Pat. No. 4,187,721, which was referred to at the beginning, and EP-A 849 568 mention that Coriolis mass flow meters can also be used to measure the instantaneous density of the flowing medium. For the invention it is therefore assumed that the devices referred to above as Coriolis mass flow meters also measure the instantaneous density of the flowing medium even though this is not always described in the individual documents, since it is self-evident.

In Coriolis mass flow meters and Coriolis mass flow/density meters, the ratio of the width D of the flow tube to the length L of the flow tube (D/L ratio) is of significance for the measurement accuracy. If a single flow tube is used, the width D is virtually equal to the nominal diameter of the pipe.

At a D/L ratio greater than approximately 0.05, the instantaneous velocity field of the medium in the flow tube may affect the measurement accuracy so that the resulting increased measurement error may no longer be negligibly small. Measurements have shown that at D/L ratios greater than 0.05, this influence of the velocity field may cause an additional error of a few per mille to one percent.

However, the minimization of the D/L ratio is limited by constraints placed on the design of the meter, namely, on the one hand, by the nominal pipe diameter specified in a concrete application and, on the other hand, by the fact that meters are required which are as short and compact as possible.

SUMMARY OF THE INVENTION

It is an object of the invention to provide a Coriolis mass flow/density meter which provides highly accurate measurement results independently of the instantaneous velocity field while being as compact in construction as possible. Another object is to provide a method of producing such measurement results.

To attain the first-mentioned object, the invention provides a Coriolis mass flow/density meter for a medium flowing through a pipe, said Coriolis mass flow/density meter comprising:

at least one flow tube having an inlet-side end and an outlet-side end, through which at least one flow tube the medium flows during operation;

a support means fixed to an inlet-side end and an outlet-side end of the flow tube such that the flow tube is capable of being vibrated;

a vibration exciter which sets the flow tube into vibration during operation;

a first measuring means positioned on the inlet-side of the flow tube for measuring the vibrations and for delivering a first measurement signal during operation;

a second measuring means positioned on the outlet-side of the flow tube for measuring the vibrations and for delivering a second measurement signal during operation;

a third measuring means for delivering a third measurement signal during operation which is representative of the instantaneous Reynolds number of the flowing medium; and evaluation electronics for delivering, during operation, a first measured value representative of mass flow rate which is derived from the first, second, and third measurement signals, and a second measured value representative of the instantaneous density of the medium, which is derived from the first and second measurement signals.

Furthermore, the invention consists in a method of generating a first measured value representative of mass flow rate by means of a Coriolis mass flow/density meter for a medium flowing through a pipe, said Coriolis mass flow/density meter comprising:

at least one flow tube having an inlet-side end and an outlet-side end, through which at least one flow tube the medium flows during operation;

a support means fixed to an inlet-side end and an outlet-side of the flow tube, such that the flow tube is capable of being vibrated;

a vibration exciter which sets the flow tube into vibration during operation, said method comprising the steps of:

sensing the vibrations of the flow tube and generating a first measurement signal representative of inlet-side vibrations and a second measurement signal representative of outlet-side vibrations for developing an intermediate value representative of an uncorrected mass flow rate;

generating a third measurement signal representative of an Reynolds number of the flowing medium by means of the intermediate value and by means of a fourth measurement signal representative of a dynamic viscosity of the medium; and correcting the intermediate value by means of a correction value derived from the third measurement signal.

In a first embodiment of the Coriolis mass flow/density meter according to the invention, the evaluation electronics provide a correction value derived from the third measurement signal.

In a second embodiment of the Coriolis mass flow/density meter according to the invention, the evaluation electronics provide the correction value by means of a constant correction value for laminar flow determined by calibration, by means of a constant correction value for turbulent flow determined by calibration, and by means of an interpolated correction value determined according to an interpolation function lying between the two constant correction values.

In a third embodiment of the Coriolis mass flow/density meter according to the invention, the evaluation electronics comprise a table memory in which Reynolds-number-dependent digitized correction values are stored, and which provides the correction value by means of a digital memory access address formed on the basis of the third measurement signal.

In a fourth embodiment of the Coriolis mass flow/density meter according to the invention, the evaluation electronics provide an intermediate value derived from the first and second measurement signals which is representative of an uncorrected mass flow rate.

In a fifth embodiment of the Coriolis mass flow/density meter according to the invention, the evaluation electronics deliver the first measured value in response to the intermediate value and the correction value.

In a sixth embodiment of the Coriolis mass flow/density meter according to the invention, the Coriolis mass flow/density meter comprises a fourth measuring means which measures a dynamic viscosity of the medium and delivers a fourth measurement signal representative of said dynamic viscosity.

In a seventh embodiment of the Coriolis mass flow/density meter according to the invention, the third measuring means delivers the third measurement signal in response to the uncorrected intermediate value and the fourth measurement signal.

In an eighth embodiment of the Coriolis mass flow/density meter according to the invention, the fourth measuring means measures a kinematic viscosity of the medium and delivers a fifth measurement signal representative of said kinematic viscosity.

In a ninth embodiment of the Coriolis mass flow/density meter according to the invention, the fourth measuring means delivers the fourth measurement signal in response to the second measured value and the fifth measurement signal.

In a tenth embodiment of the Coriolis mass flow/density meter according to the invention, the vibration exciter comprises a coil which is supplied with excitation energy and from whose current and/or voltage the fourth measuring means derives the fourth measurement signal and/or the fifth measurement signal.

In an eleventh embodiment of the Coriolis mass flow/density meter according to the invention, the fourth measuring means derives the fourth measurement signal and/or the fifth measurement signal from a pressure difference measured along the pipe.

In a first embodiment of the method according to the invention, the fourth measurement signal is derived from a current and/or a voltage of an excitation energy supplied to the vibration exciter.

In a second embodiment of the method according to the invention, the fourth measurement signal is derived from a pressure difference measured along the pipe.

One advantage of the invention is that even at a D/L ratio greater than 0.05, the Coriolis mass flow/density meter provides a mass flow value in which the effect of the instantaneous velocity field on measurement accuracy has been compensated.

BRIEF DESCRIPTION OF THE DRAWINGS

The invention will become more apparent from the following description of embodiments when taken in conjunction with the accompanying drawings. Like parts are designated by like reference characters throughout the figures; reference characters that were already introduced are omitted in subsequent figures for the sake of clarity. In the drawings:

FIG. 3 is a schematic block diagram of a subcircuit which serves to derive a sufficiently accurate mass flow value from an uncorrected mass flow value using a correction value;

FIG. 4 is a schematic block diagram of a subcircuit which derives a mass flow correction value from a measured Reynolds number;

DETAILED DESCRIPTION OF THE PREFERRED EMBODIMENTS

Figure 1:
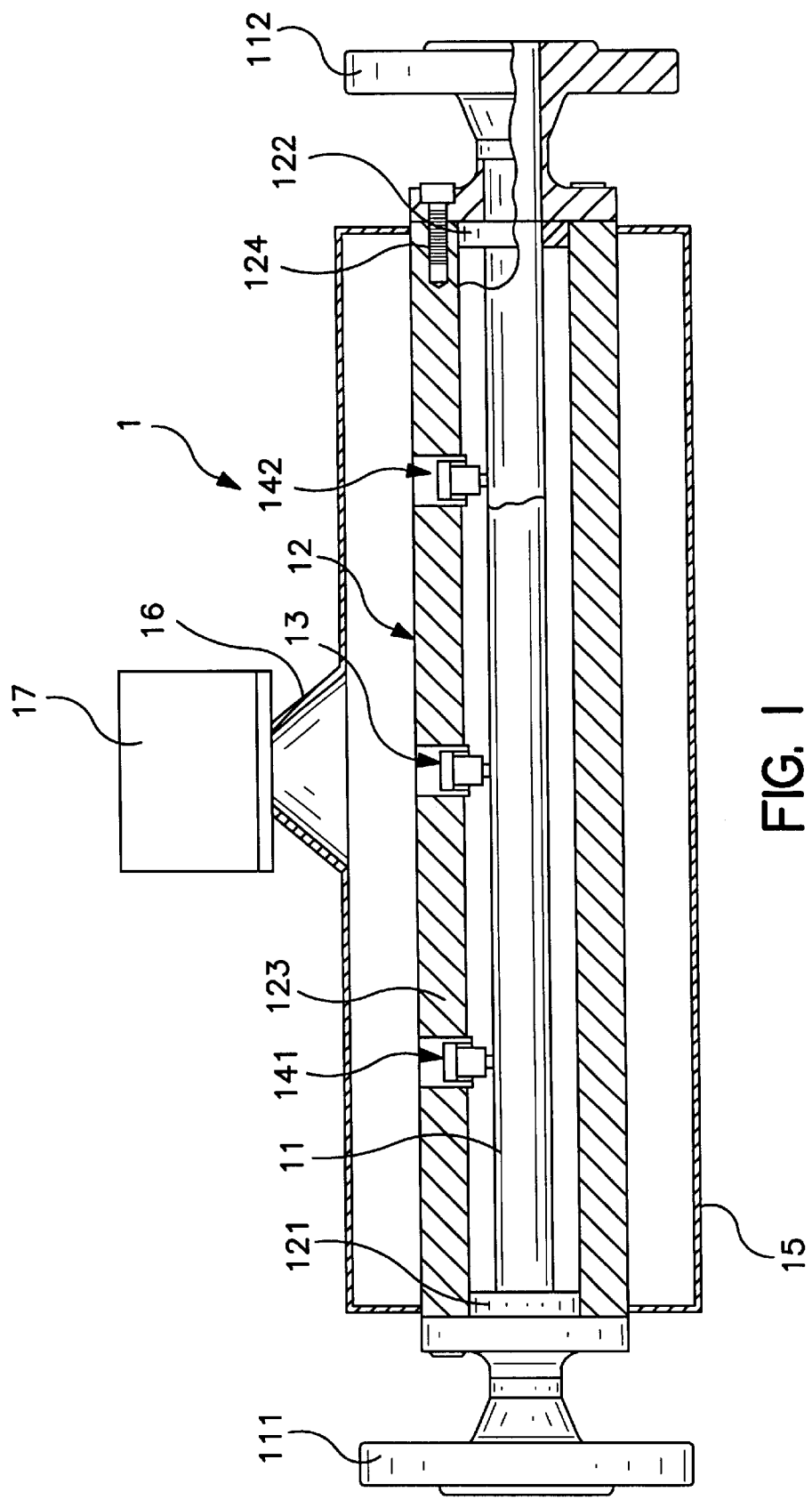
FIG. 1 is vertical longitudinal view, partially in section, of a mass flow sensor of a Coriolis mass flow/density meter.

Referring now to FIG. 1, there is shown a vertical longitudinal view, partially in section, of a mass flow sensor 1 of a Coriolis mass flow/density meter with a single straight flow tube 11, which has an inlet-side first end and an outlet-side second end.

The first end of the flow tube 11 is provided with a first flange 111, and the second end with a second flange 112, so that the mass flow sensor 1 can be inserted in a pressure-tight manner in a pipe through which a medium flows during operation.

The mass flow sensor 1 further comprises a support means 12 with a first end plate 121 fixed to the first end of the flow tube 11, a second end plate 122 fixed to the second end of the flow tube 11, and a support tube 123 inserted between the first and second end plates 121, 122. The end plates 121, 122 are connected with the flow tube 11 and the support tube 123 in a rigid and pressure-tight manner, particularly in a vacuum-tight manner. The flow tube 11 is thus mounted in a lumen of the support tube 123 between the end plates 121, 122 in a self-supporting manner, so that it can be set into vibration.

The joints between the flow tube 11 and the end plates 121, 122 and the flanges 111, 112 and the joints between the end plates 121, 122 and the support tube 123 may be welded or soldered joints, for example; the end plates 121, 122 may also be attached to the support tube 123 by means of screws, one of which, 124, is shown in FIG. 1. It is also possible to form the two end plates 121, 122 integrally with the support tube 123.

Besides mass flow sensors of the type shown in FIG. 1, mass flow sensors with two straight flow tubes are commonly used.

Instead of straight flow tubes, however, all other forms of flow tubes described in connection with Coriolis mass flow/density meters, particularly U- or omega-shaped or spiraled flow tubes, can be employed. Two or more flow tubes, preferably two, may be connected in parallel or series with respect to the flow the medium. If flow tubes are connected in parallel, the ends will be fitted with suitable manifolds for separating and combining the flowing medium.

The medium may be any fluid substance, particularly liquids, gases, or vapors.

The flow tubes are preferably made of titanium, zirconium, or high-grade steel.

FIG. 1 further shows a vibration exciter 13, which is positioned within the support means 12 between flow tube 11 and support tube 123, preferably midway between the first and second end plates 121, 122. In operation, this vibration exciter 13 sets the flow tube 11 into vibration at a mechanical resonant frequency, which, in turn, is a measure of the instantaneous density of the medium.

The vibration exciter 13 may be a solenoid assembly, for example, which comprises a soft-magnetic core attached to the flow tube 11, a permanent magnet movable therein, and a coil attached to the support tube 123 and traversed in operation by a time-variable exciting current. The permanent magnet is moved by the action of the time-variable exciting current, thus setting the flow tube 11 into vibration, with the inlet-side portion and the outlet-side portion vibrating out of phase with respect to each other as the medium passes through the flow tube 11.

For an example of exciter electronics for driving the vibration exciter 13, reference is made to U.S. Pat. No. 4,801,897.

In the case of straight flow tubes, the vibrations are generally bending or flexural vibrations, which are comparable to the vibrations of a string. These bending or flexural vibrations may have torsional vibrations superimposed on them, see EP-A 849 568. Besides bending/torsional vibrations, hoop-mode vibrations are commonly excited, in which case the flow tube moves peristaltically, see U.S. Pat. No. 4,949,583.

In the case of U- or omega-shaped flow tubes, the flexural vibrations are cantilever vibrations, which are comparable to those of a tuning fork, see U.S. Pat. No. 4,187,721.

Within the support means 12, a first measuring means 141 and a second measuring means 142 are positioned at a given distance from each other along the flow tube 11 for measuring the vibrations. The measuring means 141, 142 are preferably located at equal distances from the middle of the flow tube 11 and provide a first measurement signal $x_{s1}$ and a second measurement signal $x_{s2}$, which are representative of the vibrations.

To that end, the measuring means 141, 142 comprise vibration sensors which are preferably implemented as electrodynamic vibration sensors as in U.S. Pat. No. 5,736,653, but may also be designed as optical vibration sensors, see U.S. Pat. No. 4,801,897.

The mass flow sensor 1 is protected from environmental influences by a sensor housing 15. The latter is so designed that both the support means 12 and all electric leads connected to the mass flow sensor 1 are accommodated therein, the leads being not shown for clarity of illustration.

The sensor housing 15 has a necklike transition portion 16, to which an electronics housing 17 is fixed.

In the electronics housing 17 both the above-mentioned exciter electronics and evaluation electronics 2 as well as other circuits which are also used for the operation of the Coriolis mass flow/density meter are accommodated. These circuits can be, for instance, electronics for power supplying the coriolis mass flow/density meter which are fed from an external power source, and/or communication electronics for data transmission between the Coriolis mass flow/density meter and an external signal processing unit.

If the vibratory behavior of the mass flow sensor 1 should be adversely affected by the electronics housing 17, the latter may also be located separately from the mass flow sensor 1. Then, only an electric lead will exist between the electronics housing 17 and the mass flow sensor 1, so that the electronics housing 17 and the sensor 1 are practically vibration-isolated from each other.

Figure 2:
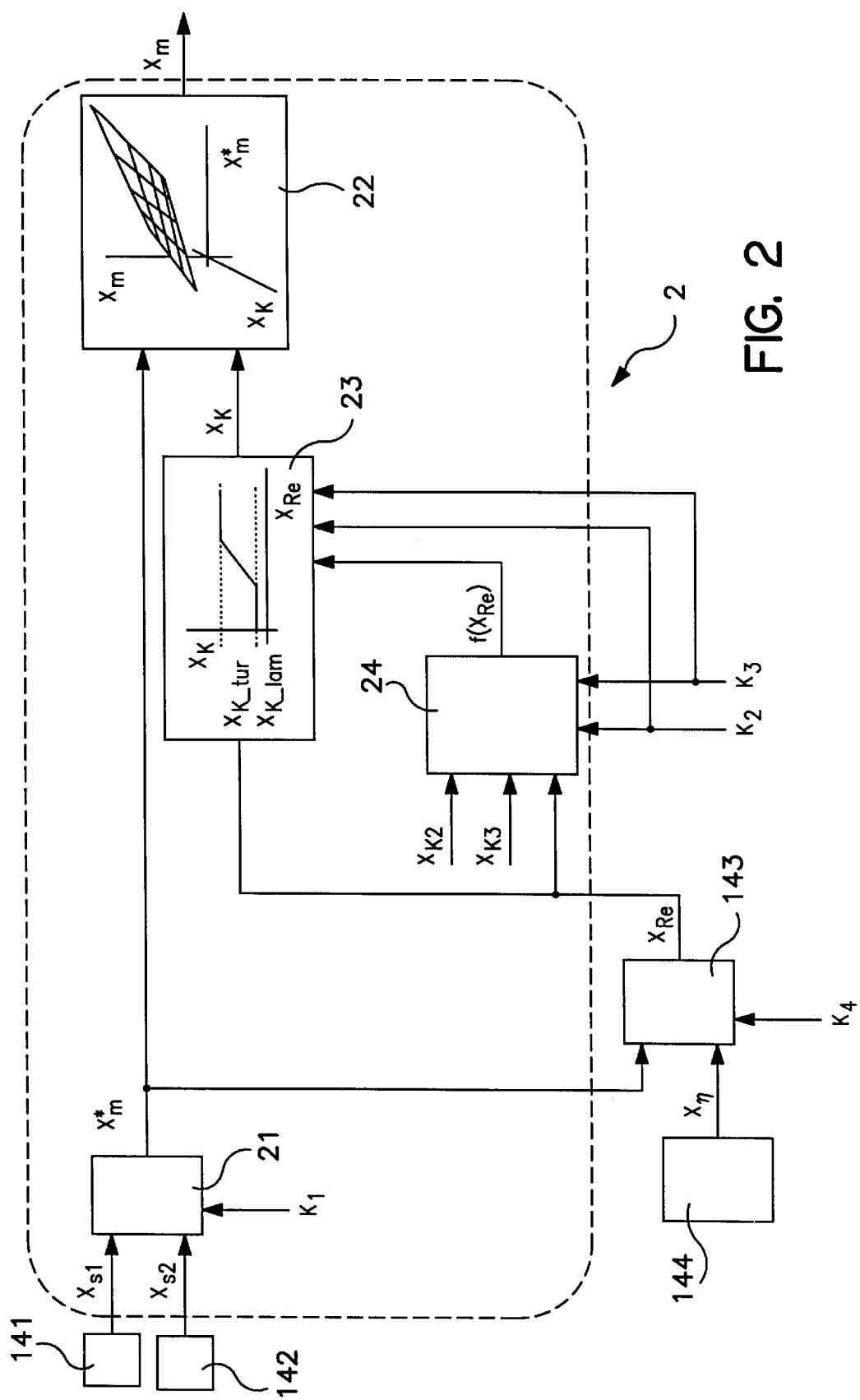
FIG. 2 is a schematic block diagram of subcircuits of the evaluation electronics of the Coriolis mass flow/density meter which serve to increase measurement accuracy.

FIG. 2 shows a block diagram of subcircuits of the evaluation electronics 2 of the Coriolis mass flow/density meter, which provide a first measured value $X_m$ representing the mass flow rate.

The measurement signals $x_{s1}$, $x_{s2}$ are fed to a measuring circuit 21 of the evaluation electronics 2. The measuring circuit 21 may, for instance, be implemented with the evaluation electronics of a Coriolis mass flow/density meter disclose in U.S. Pat. No. 5,648,616, which derive a mass flow value using an exciter circuit as disclosed in U.S. Pat. No. 4,801,897, for example. It is also possible to use other measuring electronis for Coriolis mass flow/density meters that are familar to those skilled in the art.

At large D/L ratios, however, the mass flow value determined by the measuring circuit 21 is not yet accurate enough and needs to be corrected; it will therefore be referred to herein as the intermediate value $X^*_m$, from which the measured value $X_m$ is derived, which represents the mass flow rate with sufficient accuracy.

The correction of the intermediate value $X^*_m$ is based on the following recognition by the inventors.

The mass flow rate in the flow tube 11 is given by the following equation:

$$\frac{dQ}{dt} = \frac{\pi}{4} \cdot D^2 \cdot \rho \cdot v_m \qquad (1)$$

where dQ/dt=mass flow rate

D=inside diameter of the flow tube 11 p=instantaneous density of the medium $v_m$=mean velocity of the medium flowing through the flow tube 11.

The mean velocity vm is the arithmetic mean of all velocity vectors of the flowing medium over a cross-sectional area of the flow tube 11.

The intermediate value $X^*_m$ is given by $$X^*_m = K_1 \cdot \frac{X_\varphi}{X_f} \qquad (2)$$

where $X_f$=measured value representative of the instantaneous frequency of the vibrations of the flow tube 11

$X_\varphi$=measured value representative of the instantaneous phase difference between the both measurement signals $x_{s1}$, $x_{s2}$ $K_1$=a first parameter of the Coriolis mass flow/density meter.

The parameter $K_1$ is primarily dependent on the instantaneous temperature of the medium; it may also be dependent on the instantaneous density of the medium.

For Eq. (2) it is assumed that the properties of the medium determining the parameter $K_1$, namely its instantaneous temperature and instantaneous density, are known, since they are also measured during the operation of Coriolis mass flow/density meters, cf. U.S. Pat. No. 4,768,384 for the temperature measurement and U.S. Pat. No. 4,187,721 for the density measurement.

For Eq. (2) it is further assumed that the Coriolis-induced phase difference between a flow tube vibration sensed on the inlet side and a flow tube vibration sensed on the outlet side is proportional to the instantaneous mass flow rate. This assumption supposes that all velocity fields occurring in the flow tube 11 produce the same Corriois forces at the same instantaneous flow rate. This is true with increasing accuracy as the D/L ratio decreases, since in that case all velocity fields are equal or at least very similar to each other. At great D/L ratios, particularly at ratios greater than 0.05, the correctness of that assumption decreases, resulting in an intermediate value $X^*_m$ of decreasing accuracy.

Investigations have shown that the value of the measurement accuracy depends particularly on whether the flow of the medium is laminar or turbulent.

Thus, to determine the measured value $X_m$, the intermediate value $X^*_m$ can be corrected by determining the presence of laminar flow or turbulent flow in the flow tube 11 and taking this into account in a correction value $X_K$ for the intermediate value $X^*_m$. Modifying Eq. (2) gives $$X_m = (1 + X_k) \cdot K_1 \cdot \frac{X_\varphi}{X_f} = (1 + X_k) \cdot X^*_m \qquad (3)$$

Eq. (3) is implemented with a first subcircuit 22 of the evaluation electronics 2, which is shown in FIG. 3 in block-diagram form.

The subcircuit 22 comprises a first adder 221, which forms a first sum value from the correction value $X_K$ at a first input and a value for 1 at a second input and delivers this first sum value at an output.

The subcircuit 22 further comprises a first multiplier 222 with a first input for the first sum value and a second input for the intermediate value $X^*_m$. The multiplier 222 provides at an output a first product value for $(1+X_K) \cdot X^*$, which corresponds to the measured value $X_m$.

In the invention, the correction value $X_K$ is derived from the instantaneous Reynolds number of the medium, a quantity which describes the velocity field of the flowing medium. Accordingly, the mass flow sensor 1 includes a third measuring means 143 for measuring the instantaneous Reynolds number of the medium, see FIG. 2. The measuring means 143 provides a third measurement signal $x_{Re}$, which is representative of the Reynolds number, and feeds it to the evaluation electronics 2.

In the case of laminar flow, the values of the measurement signal XRe are smaller than in the case of turbulent flow. Thus, for each width D of the flow tube 11 and the associated nominal width of the pipe, there is an upper limit value of the Reynolds number for laminar flow and a lower limit value of the Reynolds number for turbulent flow, which are not identical. These two limit values are determined during calibration.

The upper limit value of the Reynolds number for laminar flow, which is determined during calibration, is represented by a second parameter $K_2$, which is stored in the evaluation electronics 2. The lower limit value of the Reynolds number for turbulent flow, which is determined during calibration, is represented by a third parameter $K_3$, which is stored in the evaluation electronics 2.

A comparison of the measurement signal $X_{Re}$ to these two parameters $K_2$, $K_3$ shows whether laminar flow or turbulent flow is present in the flow tube 11, and provides a corresponding correction value $X_K$. This comparison is based on the following inequalities:

$$X_K = \begin{cases} X_{K2} & \text{for } x_{Re} < K_2 \\ f(x_{Re}) & \text{for } K_2 \leq x_{Re} \leq K_3 \\ X_{K3} & \text{for } K_3 < x_{Re} \end{cases} \quad (4)$$

where $X_{K2}$=constant correction value for laminar flow, determined by calibration $X_{K3}$=constant correction value for turbulent flow, determined by calibration $f(X_{Re})$=interpolation function rising monotonically from $X_{K2}$ to $X_{K3}$, whose shape can be adjusted, see below.

The result of the comparison of the measurement signal $X_{Re}$ to the two parameters $K_2$, $K_3$ according to Eq. (4) is a correction value $X_K=X_{K2}$, for laminar flow, a correction value $X_K=X_{K3}$ for turbulent flow, or an interpolated correction value $X_K=f(x_{Re})$ corresponding to interpolation function $f(X_{Re})$.

Eq. (4) is implemented with a second subcircuit 23, whose individual functional elements are shown in FIG. 4 in block-diagram form.

The subcircuit 23 comprises a first comparator 231 with a reference input for the parameter $K_2$ and with a signal input for the measurement signal $x_{Re}$. The comparator 231 provides a first binary value for $x_{Re}<K_2$, which is 1 when a instantaneous value of the measurement signal $x_{Re}$ is less than the value of the parameter $K_2$; otherwise the first binary value is 0. This first binary value is fed to a first input of a second multiplier 232. A second input of this multipier 232 receives the constant correction value for laminar flow, $X_{K2}$.

The subcircuit 23 further comprises a second comparator 233 with a reference input for the parameter $K_3$ and with a signal input for the measurement signal $x_{Re}$. The comparator 233 provides a second binary value for $x_{Re}>K_3$, which is 1 when the instantaneous value of the measurement signal $x_{Re}$ is greater than the value of the parameter $K_3$; otherwise the second binary value is 0.

The second binary value is fed to a first input of a third multiplier 234. A second input of the multiplier 234 receives the constant correction value for turbulent flow $X_{K3}$.

The subcircuit 23 further comprises a NOR gate 235 with a first input for the first binary value and with a second input for the second binary value. The NOR gate 235 provides a third binary value for $K_2 \leq x_{Re} \leq K_3$, which is 1 when the first and second binary values are 0; otherwise the third binary value is 0.

An inverter 236 following the NOR gate 235 changes the third binary value into an inverted fourth binary value, which is applied to a third input of the second multiplier 232 and to a third input of the multiplier 234.

The multiplier 232 thus provides a second product value, which is equal to the constant correction value $X_{K2}$ for laminar flow if the first and fourth binary values are 1; otherwise the second product value is 0. Analogously, the multiplier 234 provides a third product value, which is equal to the constant correction value $X_{K3}$ for turbulent flow if the second and fourth binary values are 1; otherwise the third product value is 0.

The interpolated correction value corresponding to interpolation function $f(x_{Re})$, whose formation will be described below, is fed to a first input of a fourth multiplier 237. The third binary value is presented to a second input of the multiplier 237, so that the latter provides a fourth product value, which is equal to the interpolated correction value corresponding to $f(x_{Re})$ if the third binary value is 1; if the third binary value is 0, then the fourth product value is also 0.

The second, third, and fourth product values are fed, respectively, to first, second, and third inputs of a second adder 238, which delivers a second sum value. Since only either the second or the third or the fourth product value is nonzero at any given time, the second sum value corresponds to the required correction value $X_K$.

The correction value $X_K$ can also be generated by means of a fuzzy logic provided in the subcircuit 23. To accomplish this, the first comparator 231 is replaced by a first membership function for laminar flow, the second comparator 233 by a second membership function for turbulent flow, and the NOR gate 235 by a third membership function for coexisting laminar flow and turbulent flow. These membership functions must be determined by calibration measurements and provide first, second, and third membership values which replace the first, second, and third binary values, respectively, and lie in a range between 0 and 1. The inverter 236 must be replaced by a subtracter, for example, which then deducts the third membership value from the value 1.

For flow conditions with laminar and turbulent components, the correction value $X_K$ is interpolated according to Eq. (4) using the interpolation function $f(x_{Re})$. The interpolation function $f(x_{Re})$ can be expanded in the form of a power series in the usual manner, e.g., with the parameter $K_2$ as the center, so that $$f(x_{Re}) = \sum_{n=0}^{\infty} a_n(x_{Re} - K_2)^n = a_0 + a_1(x_{Re} - K_2) + a_2(x_{Re} - K_2)^2 \quad (5)$$

Thus, the interpolation function $f(x_{Re})$ can be implemented with arbitrary accuracy using an approximation polynomial of degree n. The coefficients $a_n$ of the interpolation function $f(x_{Re})$ must be determined by calibration.

If, for example, the approximation polynomial is to be only of the first degree, i.e., if n=1, a linear relationship is obtained for the corresponding interpolation function $f(x_{Re})$:

$$f_1(x_{Re})=a_0+a_1(x_{Re}-K_2) \quad (6)$$

Using Eq. (4), $$f_1(x_{Re}) = X_{K2} + \frac{X_{K3} - X_{K2}}{K_3 - K_2}(x_{Re} - K_2) \quad (7)$$

Figure 5:
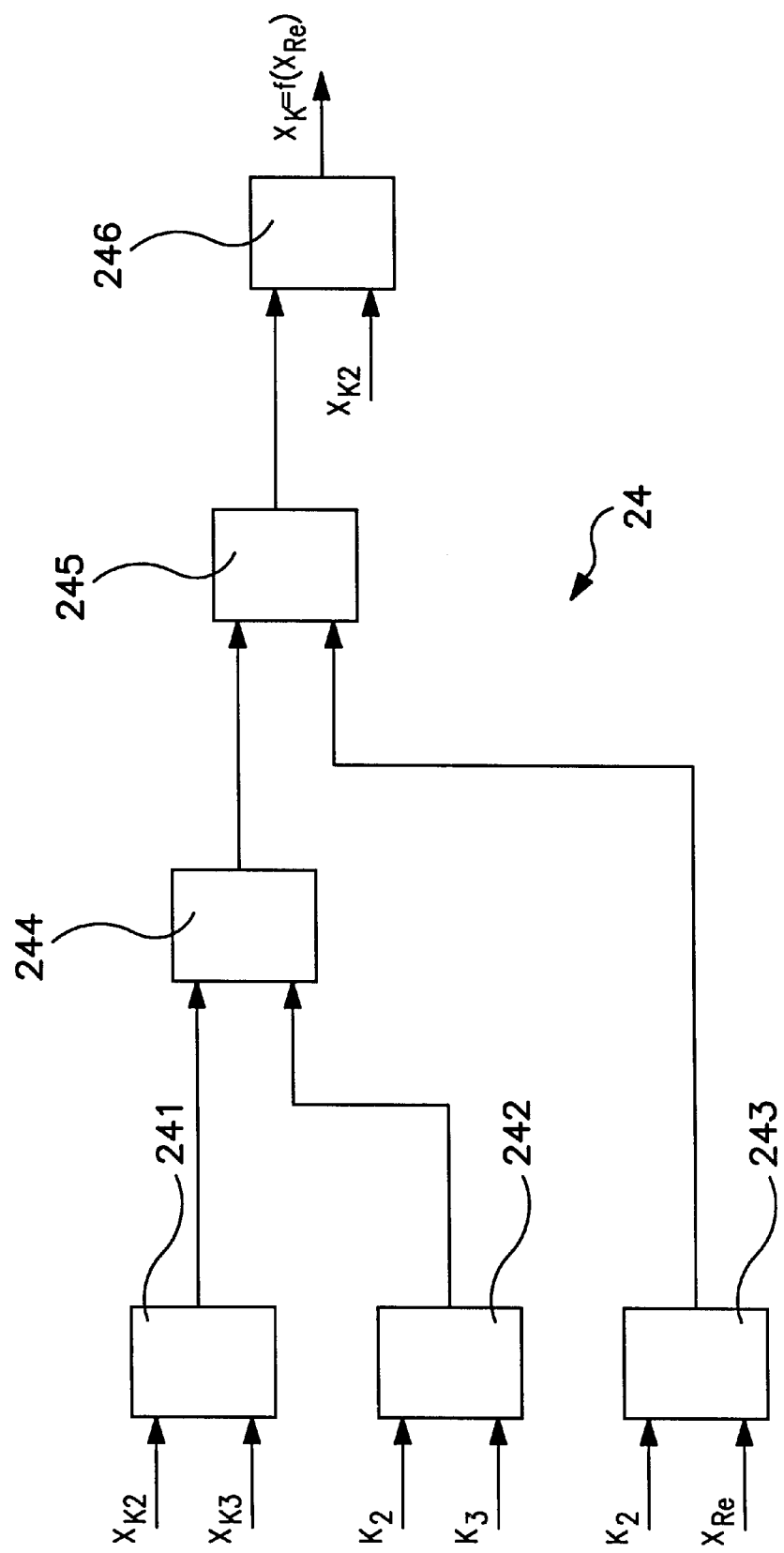
FIG. 5 is a schematic block diagram of a subcircuit which produces a mass flow correction value according to an interpolation function.

FIG. 5 shows a block diagram of a third subcircuit 24, which implements the interpolation function $f(x_{Re})$ according to Eq. (7).

The subcircuit 24 comprises a first subtracter 241 with a subtrahend input for the correction value $X_{K2}$, for laminar flow and with a minuend input for the correction value $X_{K3}$ for turbulent flow, which provides a first difference value for $X_{K2}-X_{K3}$. A second subtracter 242 with a subtrahend input for the parameter $K_2$ and a minuend input for the parameter $K_3$ provides a second difference value for $K_3-K_2$. A third subtracter 243 with a subtrahend input for the parameter $K_2$ and with a minuend input for the measurement signal $x_{Re}$ provides a third difference value for $X_{Re}-K_2$. The subcircuit 24 further includes a first divider 244 with a dividend input for the first difference value and with a divisor input for the second difference value. The divider 244 delivers a first quotient value, which corresponds to the expression $(X_{K3}-X_{K2})/(K_3-K_2)$.

A fifth multiplier 245 with a first input for the first quotient value and with a second input for the third difference value generates a fifth product value for $(x_{Re}-K_2)\cdot(X_{K3}-X_{K2})/(K_3-K_2)$, which is fed to a first input of a third adder 246. A second input of the adder 246 is supplied with the correction value $X_K2$ for laminar flow, so that the adder 246 provides a third sum value for $X_{K2}+ (x_{Re}-K_2)\cdot(X_{K3}-X_{K2})/(K_3-K_2)$. If $K_2 \leq x_{Re} \leq K_3$, i.e., under flow conditions with laminar and turbulent components, then this third sum value corresponds to the required interpolated correction value $X_K=f(x_{Re})$.

Instead of Eq. (7), any other approximation polynomial based on Eqs. (4) and (5) can be implemented with the subcircuit 24.

Instead of the subcircuits 23 and 24 shown in FIGS. 4 and 5, respectively, the evaluation electronics 2 may include a table memory containing discrete values for the correction value $X_K$. These are accessed via a digital memory address derived from the measurement signal $x_{Re}$. This digital memory address is formed by means of an analog-to-digital converter followed by an encoder. The table memory can be a programmable read-only memory, for example, an EPROM or an EEPROM.

For the measurement of the Reynolds number necessary according to Eq. (4), the following relations are used:

$$Re = \frac{1}{\eta} \cdot \frac{4}{\pi \cdot D} \cdot \frac{dQ}{dt} = \frac{1}{\zeta \cdot \rho} \cdot \frac{4}{\pi \cdot D} \cdot \frac{dQ}{dt} \quad (8)$$

where $\eta$=the dynamic viscosity of the medium $\zeta$=the kinematic viscosity of the medium.

Substituting the mean velocity vm according to Eq. (1) into Eq. (8) gives the Reynolds number as $$Re = \frac{1}{\eta} \cdot \frac{4}{\pi \cdot D} \cdot \frac{dQ}{dt} = \frac{1}{\zeta \cdot \rho} \cdot \frac{4}{\pi \cdot D} \cdot \frac{dQ}{dt} \quad (9)$$

In accordance with the invention, according to Eq. (9), either the dynamic viscosity of the medium or the kinematic viscosity is used to generate the third measurement signal $x_{Re}$, and thus to determine the correction value $X_K$, since the two viscosities can be readily converted to each other taking into account the instantaneous density $\rho$ of the medium.

Substituting the corresponding measurement signals into Eq. (9) gives the following relation for the measurement signal $x_{Re}$ if the dynamic viscosity is used:

$$x_{Re} = \frac{K_4}{x_\eta} \cdot X_m^* \quad (10)$$

where $x_\eta$=a fourth measurement signal, representative of the dynamic viscosity of the medium $K_4$ a fourth parameter, derived from the quotient $4/\pi D$.

Figure 6A:
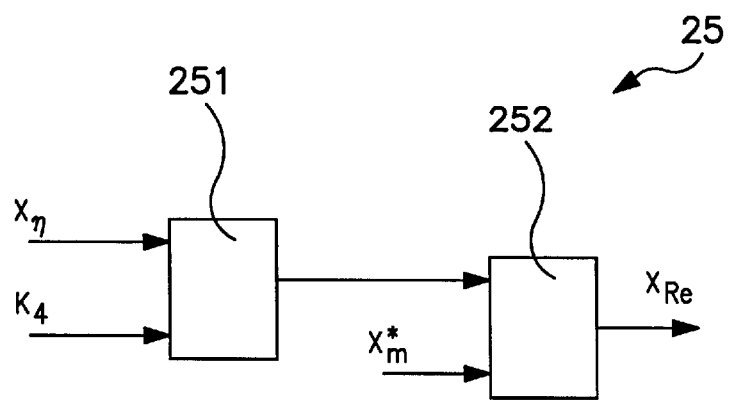
FIG. 6a is a schematic block diagram of a subcircuit which determines the Reynolds number from a measured dynamic viscosity of the medium.

Eq. (10) is implemented in the third measuring means 143 with a fifth subcircuit 25, which is shown in block-diagram form in FIG. 6a.

The subcircuit 25 comprises a second divider 251 with a dividend input for the parameter $K_4$ and with a divisor input for the measurement signal $x_\eta$. The divider 251 delivers a second quotient value for $K_4/x_\eta$, which is fed to a first input of a sixth multiplier 252. A second input of the multiplier 252 is supplied with the intermediate value $X^*_m$. The multiplier 252 thus provides a sixth product value which corresponds to the measurement signal $x_{Re}$ according to Eq. (10).

The measurement signal $x_\eta$, which is necessary according to Eq. (10) to determine the measurement signal $x_{Re}$, is generated by a further, fourth measuring means 144, see FIG. 2.

According to Eq. (8), the kinematic-viscosity and the instantaneous density of the medium can be used to determine the dynamic viscosity of the medium. Using Eq. (9) gives the measurement signal $x_\eta$ as $$x_\eta = x_{90} \cdot X_\rho \quad (11)$$

where $x_\zeta$=a fifth measurement signal, representative of the kinematic viscosity of the medium, $x_\rho$=a second measured value, representative of the instantaneous density of the medium.

Figure 6B:
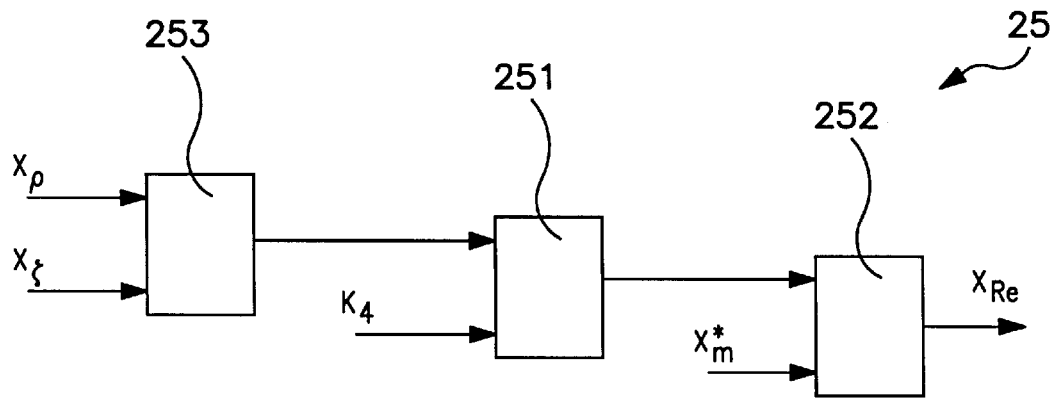
FIG. 6b is a schematic block diagram of a subcircuit which determines the Reynolds number from a measured kinematic viscosity of the medium.

In an embodiment of the invention based on Eq. (11), the measuring means 144 uses the measurement signal $x_\zeta$, which represents the kinematic viscosity of the medium, to generate the measurement signal $x_\eta$. Accordingly, the subcircuit 25, as shown in FIG. 6b in block-diagram form, comprises a seventh multiplier 253 with a first input for the measurement signal $x_{70}$ and with a second input for the measured value $X_\rho$. The multiplier 253 delivers as a product value the measurement signal $x_\eta$, which is fed to the divisor input of the second divider 251. The measured value $X_\rho$ is derived, for example, from the instantaneous vibration frequency of the flow tube, see the above-mentioned U.S. Pat. No. 4,187,721.

The measures necessary to generate the measurement signal $x_\zeta$ are explained in the following. Since the viscosity is a quantity describing the internal friction of the flowing medium, the inventors have come to the conclusion that a determination of the kinematic viscosity is possible by measuring the excitation energy supplied to the vibration exciter 13. Due to the internal friction of the medium, the vibrations of the fluid-conducting flow tube 11 are additionally damped as a function of the viscosity of the medium, particularly of the kinematic viscosity, as compared with the empty flow tube 11. To maintain the vibrations of the flow tube 11, the additional energy loss caused by friction must be compensated for by correspondingly increased excitation energy.

Therefore, in a preferred embodiment of the invention, the measurement signal $x_\zeta$ is determined using the following relation:

$$x_\zeta = K_5 \cdot (x_{exc} - K_6)^2 \quad (12)$$

where $x_{exc}$=a sixth measurement signal representative of the excitation energy supplied to the vibration exciter 13, $K_5$, $K_6$=a constant fifth parameter and a constant sixth parameter, respectively.

According to Eqs. (11) and (12), the measurement signal $x_\zeta$ is dependent exclusively on defining quantities occurring during the operation of Coriolis mass flow/density meters, namely on the measured value $X_\rho$ and on the measurement signal $x_{exc}$, which is representative of the excitation energy.

Figure 7:
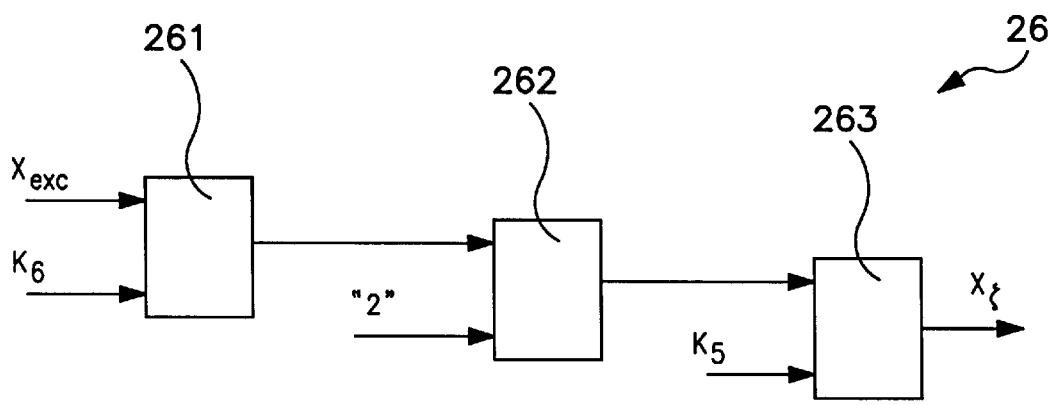
FIG. 7 is a schematic block diagram of a subcircuit which determines the kinematic viscosity of the medium from a measured excitation energy of the vibration exciter.

In an embodiment of the invention based on Eq. (12), the measuring means 144 comprises a sixth subcircuit 26, which is shown in FIG. 7 in block-diagram form.

The subcircuit 26 comprises a fourth subtracter 261 with a minuend input for the measurement signal $x_{exc}$, which represents the excitation energy, and with a subtrahend input for the parameter $K_6$. The subtracter 261 forms a fourth difference value for $x_{exc}-K_6$ and feeds it to a signal input of a first exponentiator 262. An exponent input is supplied with the value 2, so that the exponentiator 262 changes the fourth difference value into a first power value for $(x_{exc}-K_6)^2$. The power value is fed to a first input of an eighth multiplier 263, which multiplies it by the parameter $K_5$ applied at a second input to form an eighth product value for $K_5 \cdot (x_{exc}-K_6)^2$, which corresponds to the measurement signal $x_\zeta$.

The measurement signal $x_{exc}$, which represents the excitation energy, is formed by a current and/or voltage measurement or by an impedance measurement at the vibration exciter. In one embodiment of the invention, a voltage-to-current converter associated with the vibration exciter 13, which is formed by a solenoid assembly, converts an exciting voltage applied to the coil into a current proportional thereto, which, in turn, is converted by a subsequent root-mean-square converter into an rms value. The latter is then the measurement signal representative of the excitation energy, $X_{exc}$.

Instead of measuring the excitation energy, a further possibility of determining the kinematic viscosity of the medium is to measure and evaluate a pressure difference over a suitable measuring length along the pipe or along the flow tube 11.

In the case of predominantly laminar flow along the measuring length, the kinematic viscosity is $$\zeta = \frac{2\pi \cdot D^4}{L} \cdot \left(\frac{dQ}{dt}\right)^{-1} \cdot \Delta p \quad (13)$$

and in the case of predominantly turbulent flow, the kinematic viscosity is $(\Delta p)^4$ $$v = 0,3^{-4} \cdot \frac{D^{19}}{L^4} \cdot \rho^3 \cdot \left(\frac{dQ}{dt}\right)^{-7} \cdot (\Delta p)^4 \quad (14)$$

where

L=the measuring length $\Delta p$=the pressure difference over the measuring length.

Eq. (13) is based on the well-known Hagen-Poiseuille law, while Eq. (14) is determined empirically. With respect to the pressure difference, both equations are monotonically rising functions which have a single point of intersection.

Therefore, in a further embodiment of the invention, the measurement signal $x_\zeta$ is determined using the following relations, which are obtained by substituting the respective measurement signals into Eqs. (13) and (14):

$$x_\zeta = \begin{cases} X_{\zeta 1} = K_7 \cdot \dfrac{x_{\Delta p}}{X_m^*} & \text{for } X_{\zeta 1} < X_{\zeta 2} \\ X_{\zeta 2} = K_8 \cdot \dfrac{(x_{\Delta p})^4}{(X_m^*)^7} \cdot (X_\rho)^3 & \text{for } X_{\zeta 2} \le X_{\zeta 1} \end{cases} \quad (15)$$

where $X_{\zeta 1}$=a measured value representative of the kinematic viscosity of the medium in the case of laminar flow, $X_{\zeta 2}$=a measured value representative of the kinematic viscosity of the medium in the case of turbulent flow, $X_{\Delta p}$=a seventh measurement signal, represenative of the pressure difference, $K_7$=a seventh parameter, derived from the quotient $2\pi D^4/L$ according to Eq. (13)

$K_8$=an eighth parameter, derived from the quotient $0.3^{-4} D^{19}/L^4$ according to Eq. (14).

According to Eq. (15), the valid value for the measurement signal $x_\zeta$ is always the smaller one of the two measured values $X_{\zeta 1}$ for laminar flow and $X_{\zeta 2}$ for turbulent flow.

According to Eq. (15), the measurement signal $x_\zeta$ is dependent on defining quantities occurring during the operation of Coriolis mass flow/density meters, namely on the intermediate value $X^*_m$ and on the second measured value $X_\rho$. In addition, the measurement signal $x_\zeta$ is dependent on a further defining quantity, namely on the measurement signal $x_{\Delta p}$, which is representative of the pressure difference and is determined during operation.

Figure 8A:
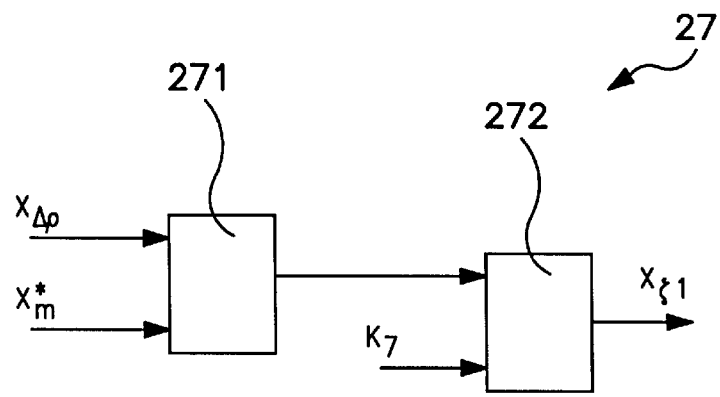
FIG. 8a is a schematic block diagram of a subcircuit which derives measured values for the kinematic viscosity in laminar flow from a pressure difference measured in the direction of flow.
Figure 8B:
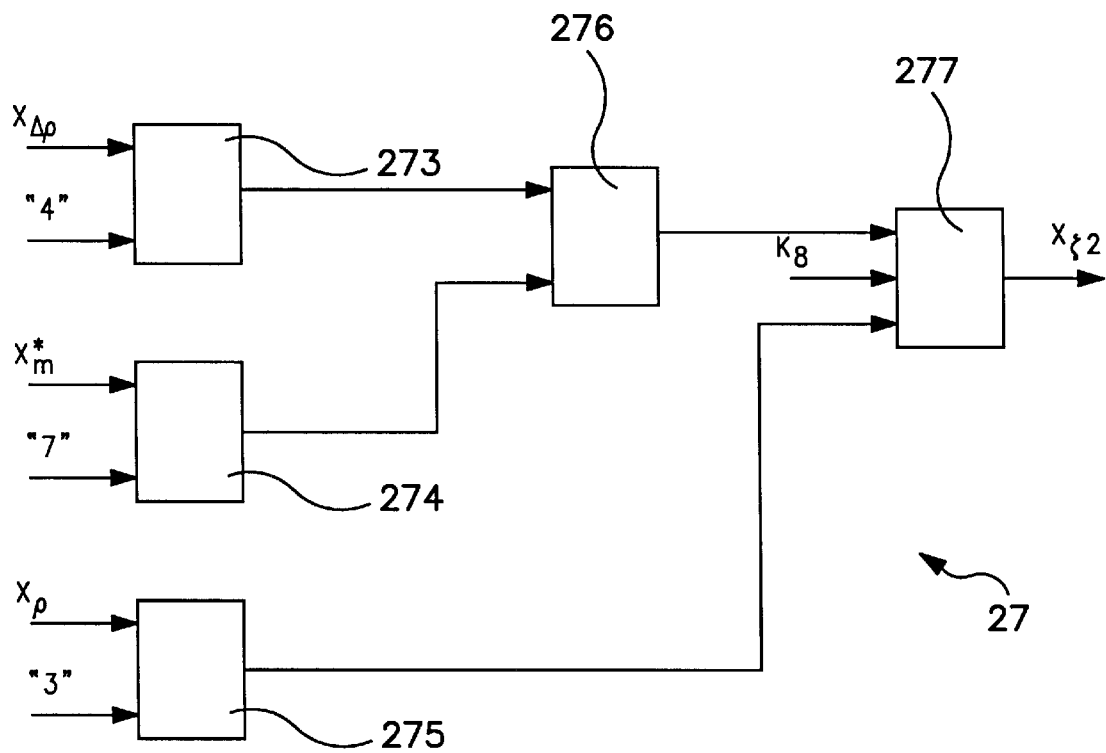
FIG. 8b is a schematic block diagram of a subcircuit which derives measured values for the kinematic viscosity in turbulent flow from a pressure difference measured in the direction of flow.
Figure 9:
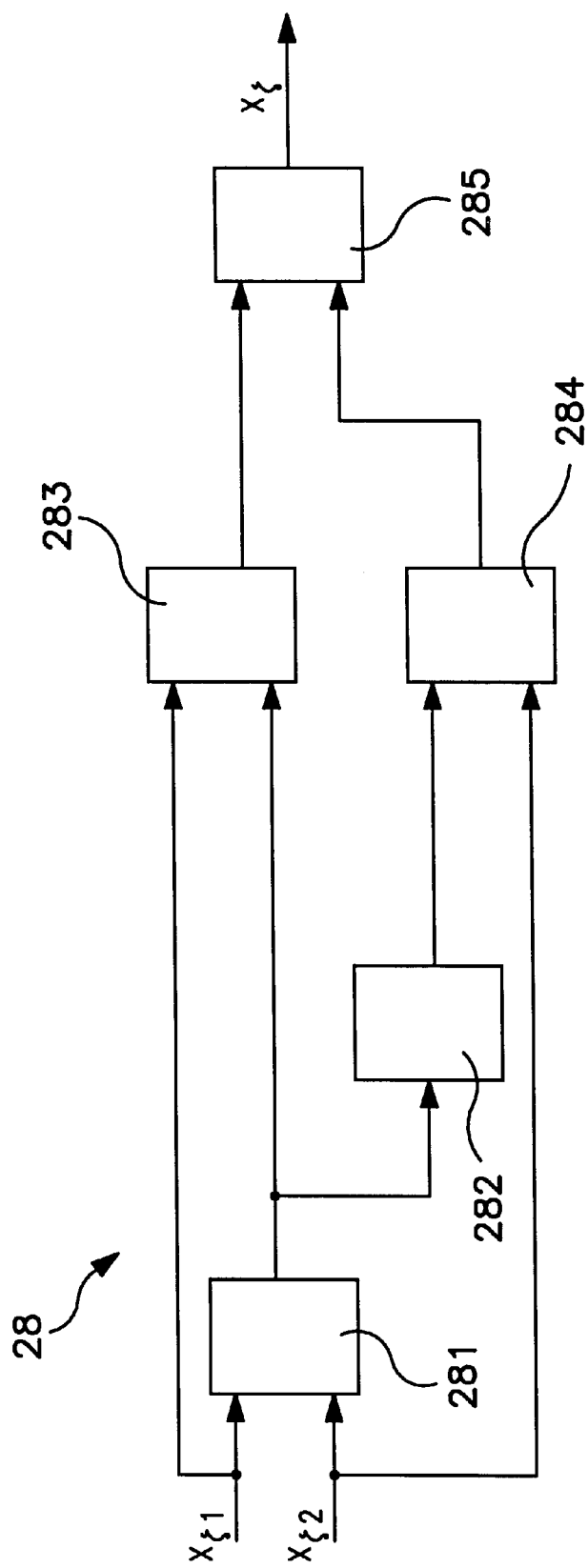
FIG. 9 is a schematic block diagram of a subcircuit for determining the instantaneous kinematic viscosity of the medium.

In a further embodiment of the invention, to implement Eq. (15), the measuring means 144 comprises a seventh subcircuit 27 as shown in FIGS. 8a, 8b and an eighth subcircuit 28 as shown in FIG. 9.

The subcircuit 27 serves to generate the two measured values representative of the viscosity of the medium, $X_{\zeta 1}$ and $X_{\zeta 2}$. It comprises a third divider 271 with a dividend input for the measurement signal $x_{\Delta p}$ and with a divisor input for the intermediate value $X^*_m$. The divider 271 provides a third quotient value for $X_{\Delta p}/X^*_m$, which is fed to a first input of a ninth multiplier 272. A second input of the multiplier 272 is supplied with the parameter $K_7$, so that the multiplier 272 delivers a ninth product value for $K_7 \cdot x_{\Delta p}/X^*_m$, which corresponds to the measured value representative of the kinematic viscosity of the medium in the case of laminar flow, $X_{\zeta 1}$.

The subcircuit 27 further comprises a second exponentiator 273 with a signal input for the measurement signal $x_{\Delta p}$ and with an exponent input for the value 4. The exponentiator 273 provides a second power value for $(X_{\Delta p})^4$ and feeds it to a dividend input of a fourth divider 276.

The subcircuit 27 further comprises a third exponentiator 274 with a signal input for the intermediate value $X^*_m$ and with an exponent input for the value 7. The exponentiator 274 provides a third power value for $(X^*_m)^7$. A fourth exponentiator 275 with a signal input for the measured value $X_\rho$ and with an exponent input for the value 3 delivers a fourth power value for $(X_\rho)^3$.

The third power value $(X^*_m)^7$ is fed to a divisor input of the fourth divider 276, while the fourth power value $(X_\rho)^3$ is presented to the first input of a tenth multiplier 277. The multiplier 277 has a second input for the parameter $K_8$ and a third input for a fourth quotient value for $(X_{\Delta p})^4/(X^*_m)^7$, which is provided by the divider 276. The multiplier 277 thus delivers a tenth product value for $K_8 \cdot (x_\rho)^3 \cdot (x_{\Delta p})^4/(X^*_m)^7$, which corresponds to the measured value representative of the kinematic viscosity of the medium in turbulent flow, $X_{\zeta 2}$.

The subcircuit 28, shown in FIG. 9, serves to implement the two inequalities according to Eq. (15). The subcircuit 28 comprises a third comparator 281 with a first input for the ninth product value and with a second input for the tenth product value. The comparator 281 provides a fifth binary value for $K_7 x_{\Delta p}/X^*_m < K_8 \cdot (X_\rho)^3 \cdot (X_{\Delta p})^4/(X^*_m)^7$, which is 1 if the ninth product value is less than the tenth product value; otherwise the fifth binary value is 0.

The fifth binary value is fed to a second inverter 282 and to a first input of a eleventh multiplier 283. A second input of the multiplier 283 is supplied with the ninth product value, so that the multiplier 283 delivers an eleventh product value, which is equal to the ninth product value if the fifth binary value is 1, or which is 0 if the fifth binary value is 0.

The inverter 282 provides a sixth binary value, which is inverted with respect to the fifth binary value and is applied to the first input of a twelfth multiplier 284. A second input of the multiplier 284 is supplied with the tenth product value, so that the multiplier 284 provides a twelfth product value, which is equal to the tenth product value if the sixth binary value is 1, or which is 0 if the sixth binary value is 0.

The eleventh product value is fed to a first input of a fourth adder 285, and the twelfth product value is fed to a second input of the adder 285. Since only one of the two product value is nonzero at any given time, a fourth sum value provided by the adder 285 is equal to the measurement signal $x_\zeta$.

Any difference between the kinematic viscosity determined according to Eq. (15) and the actual kinematic viscosity in the flow tube 11, which is due, for example, to the effect of temperature differences in the medium, can be readily compensated for by suitable temperature measurements.

The subcircuits 21, 22, 23, 24, 25, 26, 27, and 28 are assumed to be analog computing circuits but can also be implemented, at least in part, as digital computing circuits using discrete components or a microprocessor.

If the operation of the subcircuits 22 . . . 28, which operate virtually in parallel, is time-uncritical, like functions, such as add, subtract, multiply, divide, and exponentiate, can be combined using multiplexers and demultiplexers in such a way that each of these functions is implemented in a subcircuit only once and that the individual computed values are generated by sequential application of the corresponding input values to the inputs.

What is claimed is:

1. A Coriolis mass flow/density meter for a medium flowing through a pipe, said Coriolis mass flow/density meter comprising:
   at least one flow tube for conducting said medium, said flow tube having an inlet-side end and an outlet-side end;
   support means fixed to said inlet-side end and said outlet-side end of the flow tube such that the at least one flow tube is capable of being vibrated;
   vibration exciting means for vibrating said at least one flow tube to generate inlet-side bending vibrations and outlet-side bending vibrations;
   measuring means for detecting said inlet-side and outlet-side bending vibrations of said at least one flow tube, said measuring means delivering a first measurement signal representative of said inlet-side bending vibrations of the flow tube and a second measurement signal representative of said outlet-side bending vibrations of the flow tube;
   means for delivering a third measurement signal during operation from which an instantaneous Reynolds number of the flowing medium can be derived; and
   evaluation electronics for receiving said first, second and third measurement signals and delivering a measured value representative of mass flow rate which is derived from said first, second, and third measurement signals.

2. A Coriolis mass flow/density meter as claimed in claim 1 wherein the evaluation electronics comprise means for deriving a correction value from the third measurement signal.

3. A Coriolis mass flow/density meter as claimed in claim 2 wherein the evaluation electronics derive the correction value from the third measurement signal using a laminar flow constant correction value determined by calibration, a turbular flow constant correction value determined by calibration, and an interpolated correction value determined according to an interpolation function lying between the laminar flow constant correction value and the turbulent flow constant correction value.

4. A Coriolis mass flow/density meter as claimed in claim 2 wherein the evaluation electronics comprise a table memory in which Reynolds-number-dependent digitized correction values are stored, and a digital memory access address formed on the basis of the third measurement signal.

5. A Coriolis mass flow/density meter as claimed in claim 4 wherein the evaluation electronics provide an intermediate value derived from the first and second measurement signals which is representative of an uncorrected mass flow rate.

6. A Coriolis mass flow/density meter as claimed in claim 1 wherein the evaluation electronics derive from the first and second measurement signals an intermediate value representative of an uncorrected mass flow rate.

7. A Coriolis mass flow/density meter as claimed in claim 6 wherein the evaluation electronics derive a correction value from the third measurement signal and deliver the first measured value in response to the intermediate value and the correction value.

8. A Coriolis mass flow/density meter as claimed in claim 1 wherein the Coriolis mass flow/density meter comprises means for determining a viscosity of the medium and delivering a fourth measurement signal which is representative of said viscosity.

9. A Coriolis mass flow/density meter as claimed in claim 8 wherein said means for delivering a third measurement signal delivers the third measurement signal in response to said uncorrected intermediate value and said fourth measurement signal.

10. A Coriolis mass flow/density meter as claimed in claim 8 wherein said means for determining a viscosity measures a kinematic viscosity of the medium and delivers a fifth measurement signal representative of said kinematic viscosity.

11. A Coriolis mass flow/density meter as claimed in claim 10 wherein said means for determining a viscosity delivers the fourth measurement signal in response to the measured value and the fifth measurement signal.

12. A Coriolis mass flow/density meter as claimed in claim 10 wherein said means for determining a viscosity of the medium delivers the fourth measurement signal in response to the second measured value and the fifth measurement signal.

13. A Coriolis mass flow/density meter as claimed in claim 10 wherein the vibration exciting means comprises a coil which is supplied with excitation energy from which said means for determining a viscosity derives the fourth measurement signal and/or the fifth measurement signal.

14. A Coriolis mass flow/density meter as claimed in claim 10 wherein said means for determining a viscosity derives the fourth measurement signal and/or the fifth measurement signal from a pressure difference measured along the pipe.

15. A Coriolis mass flow/density meter as claimed in claim 8 wherein the vibration exciting means comprises a coil which is supplied with excitation energy from which said means for determining a viscosity of the medium derives the fourth measurement signal.

16. A Coriolis mass flow/density meter as claimed in claim 8 wherein said means for determining a viscosity of the medium derives the fourth measurement signal from a pressure difference measured along the pipe.

17. A Coriolis mass flow/density meter as claimed in claim 1 wherein the evaluation electronics further comprise comparing means for comparing the third measurement signal with a first limit value representative of laminar flow of the medium.

18. A Coriolis mass flow/density meter as claimed in claim 17 wherein the evaluation electronics derive a correction value from the third measurement signal using a laminar flow constant correction value determined by calibration, a turbular flow constant correction value determined by calibration, and an interpolated correction value determined according to an interpolation function lying between the laminar flow constant correction value and the turbulent flow constant correction value.

19. A Coriolis mass flow/density meter as claimed in claim 18 wherein the evaluation electronics further comprise comparing means for comparing the third measurement signal with a second limit value representative of turbulent flow of the medium.

20. A Coriolis mass flow/density meter as claimed in claim 1 wherein the at least one flow tube is a straight tube.

21. A Coriolis mass flow/density meter as claimed in claim 1 wherein the at least one flow tube is a curved tube.

22. A method of generating a measured value representative of mass flow rate by means of a Coriolis mass flow/density meter for a medium flowing through a pipe, said Coriolis mass flow/density meter comprising:
   at least one flow tube having an inlet-side end and an outlet-side end, wherein the medium flows through the at least one flow tube during operation;
   a support means fixed to said inlet-side end and said outlet-side of the at least one flow tube, such that the at least one flow tube is capable of being vibrated;
   a vibration exciter which sets the at least one flow tube into vibration during operation, said method comprising the steps of:
   sensing vibrations of the at least one flow tube and generating a first measurement signal representative of inlet-side bending vibrations and a second measurement signal representative of outlet-side bending vibrations for developing an intermediate value representative of an uncorrected mass flow rate;
   generating a third measurement signal representative of a Reynolds number of the flowing medium using the intermediate value and a fourth measurement signal representative of a viscosity of the medium; and
   correcting the intermediate value using a correction value derived from the third measurement signal.

23. A method as claimed in claim 22 wherein the fourth measurement signal is derived from a current and/or a voltage of an excitation energy suppling to the vibration exciter.

24. A Coriolis mass flow/density meter as claimed in claim 23 wherein the vibrations being detected by said means for detecting vibrations of the flow tube are cantilever vibrations.

25. A method as claimed in claim 22 wherein the fourth measurement signal is derived from a pressure difference measured along the pipe.

26. A Coriolis mass flow meter for a medium flowing through a pipe, said Coriolis mass flow meter comprising:
   at least one flow tube having an inlet-side end and an outlet-side end, wherein the medium flows through said at least one flow tube;
   a support fixed to said inlet-side end and said outlet-side end of the flow tube such that the at least one flow tube is capable of being vibrated;
   a vibration exciter which generates inlet-side and outlet-side bending vibrations;
   means for delivering a signal which is representative of an instantaneous Reynolds number of the flowing medium; and
   evaluation electronics configured to receive said signal and deliver a value representative of mass flow rate which is derived from said signal.

27. A method of measuring a mass flow rate of a medium flowing through at least one flow tube of a Coriolis mass flow meter, said method comprising the steps of:
   vibrating said at least one flow tube conducting the medium;
   sensing vibrations of the flow tube and generating a measurement signal representative of inlet-side bending vibrations and a measurement signal representative of outlet-side bending vibrations:
   determining a viscosity of the medium and generating a measurement signal representative of the viscosity; and
   deriving from said measurement signal representative of inlet-side bending vibrations, said measurement signal representative of outlet-side bending vibrations, and said measurement signal representative of the viscosity a measured value representative of the mass flow rate.

28. The method as claimed in claim 24 wherein the step of determining the viscosity of the medium further comprises the steps of generating a measurement signal representative of excitation energy supplied to the flow tube for vibrating and deriving said measurement signal representative of the viscosity from said measurement signal representative of the excitation energy.

29. The method as claimed in claim 24 wherein the step of deriving said measured value further comprises the step of deriving, from said measurement signal representative of inlet-side bending vibrations, said measurement signal representative of outlet-side bending vibrations, and said measurement signal representative of the viscosity, a measurement signal representative of a Reynolds number of the flowing medium.

30. The method as claimed in claim 28 wherein the step of deriving said measured value further comprises the steps of:
   deriving from said measurement signal representative of inlet-side bending vibrations and said measurement signal representative of outlet-side bending vibrations an intermediate value representative of an uncorrected mass flow rate;
   developing from said measurement signal representative of the Reynolds number a correction value for said intermediate value; and
   correcting the intermediate value by means of the correction value.

31. The method as claimed in claim 24 wherein the step of determining the viscosity of the medium comprises the step of generating a measurement signal representative of a pressure difference in the flowing medium.

* * * * *

UNITED STATES PATENT AND TRADEMARK OFFICE
CERTIFICATE OF CORRECTION

PATENT NO.    : 6,513,393 B1
DATED         : February 4, 2003
INVENTOR(S)   : Gerhard Eckert et al.

It is certified that error appears in the above-identified patent and that said Letters Patent is hereby corrected as shown below:

<u>Title page,</u>
Item [73], please add the following Assignee:
-- [73] Assignee: Endress + Hauser Flowtec AG, Reinach (Switzerland) --

Signed and Sealed this

Fifteenth Day of April, 2003

JAMES E. ROGAN
*Director of the United States Patent and Trademark Office*